United States Patent [19]

Smith

[11] Patent Number: 5,087,246
[45] Date of Patent: Feb. 11, 1992

[54] DILATION CATHETER WITH FLUTED BALLOON

[75] Inventor: Charles E. Smith, Lowell, Mass.

[73] Assignee: C. R. Bard, Inc., Murray Hill, N.J.

[21] Appl. No.: 291,566

[22] Filed: Dec. 29, 1988

[51] Int. Cl.⁵ .................................. A61M 29/00
[52] U.S. Cl. ................................ 604/96; 604/103
[58] Field of Search ............... 128/344, 348.1, 4; 604/96, 103, 97, 98, 100; 600/18

[56] References Cited

U.S. PATENT DOCUMENTS

| | | | |
|---|---|---|---|
| 3,960,143 | 6/1976 | Terada | 128/4 |
| 4,018,231 | 4/1977 | Wallace | 604/100 X |
| 4,195,637 | 4/1980 | Grüntzig et al. | 604/97 |
| 4,276,874 | 7/1981 | Wolvek et al. | 604/96 |
| 4,292,974 | 10/1981 | Fogarty et al. | 128/344 |
| 4,323,071 | 4/1982 | Simpson et al. | 604/98 |
| 4,327,709 | 5/1982 | Hanson et al. | 604/96 X |
| 4,346,698 | 8/1982 | Hanson et al. | 604/103 |
| 4,490,421 | 12/1984 | Levy | 428/35 |
| 4,552,127 | 11/1985 | Schiff | 604/96 X |
| 4,846,174 | 7/1989 | Willard et al. | 604/95 X |
| 4,848,344 | 7/1989 | Sos et al. | 604/96 X |
| 4,968,300 | 11/1990 | Moutafis et al. | 604/96 |

Primary Examiner—C. Fred Rosenbaum
Assistant Examiner—Corrine Maglione
Attorney, Agent, or Firm—Wolf, Greenfield & Sacks

[57] ABSTRACT

A balloon dilatation catheter is provided with a fluted balloon defining at least three wings. When the balloon collapses, it tends to assume the fluted configuration which defines a lower profile better adapted to pass through narrow channels, such as in endoscopes and guide catheters. The balloon is formed from a polymeric material in a method that involves the steps of tensioning the balloon to cause it to form flutes while maintaining its interior under vacuum and subjecting the balloon, while so held, to heat and, thereafter, cooling the balloon while maintaining it in its tensioned, fluted configuration.

7 Claims, 4 Drawing Sheets

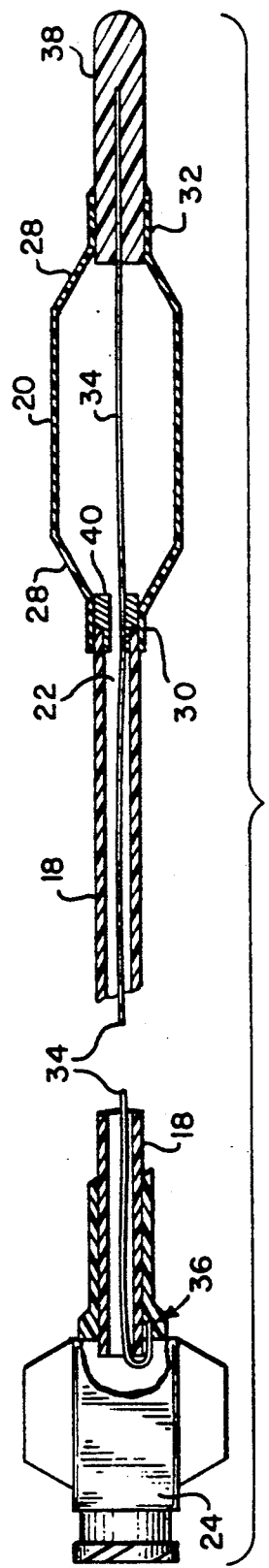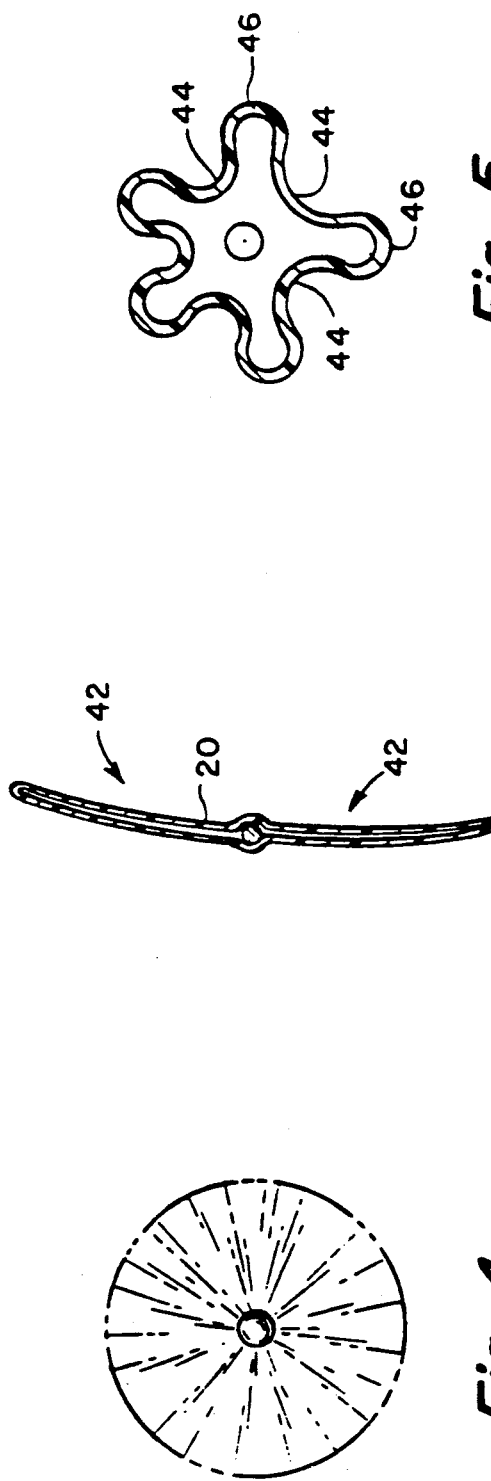
Fig. 3
Fig. 5
Fig. 2 (PRIOR ART)
Fig. 4

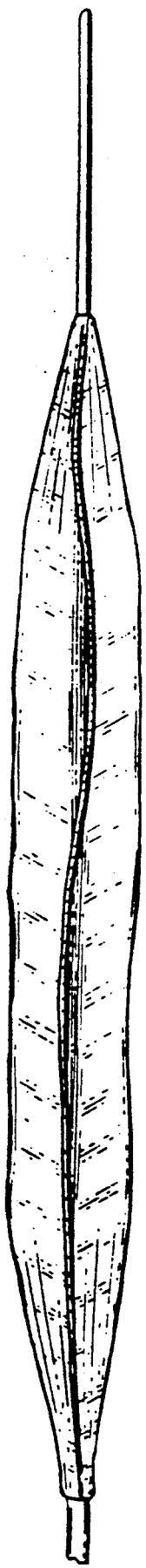
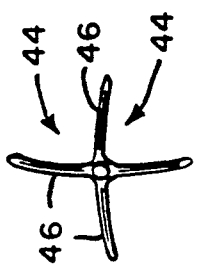
Fig. 6
Fig. 6A

DILATION CATHETER WITH FLUTED BALLOON

FIELD OF THE INVENTION

This invention relates to balloon catheters used for dilatation procedures.

BACKGROUND OF THE INVENTION

Balloon dilatation catheters are used for a wide variety of medical procedures, typically to enlarge a body lumen that has become obstructed. For example, balloon dilatation catheters commonly are used in angioplasty procedures to enlarge the lumen of a blood vessel constricted or stenosed by arteriosclerosis. Recent years have seen significant advances in percutaneous transluminal coronary angioplasty in which a dilatation catheter having a relatively inelastic polymeric balloon on its distal end is advanced percutaneously into the patient's arterial system and into the coronary artery to be treated. The balloon is inserted into the stenosis and is inflated to effect the dilatation. Such catheters also are used to perform angioplasty procedures on peripheral arteries as well. U.S. Pat. No. 4,195,637 to Gruntzig discloses such angioplasty catheters. Balloon dilatation catheters also are used to dilate other body lumens, such as, for example, in the esophageal tract, blood vessels and the like.

Balloon dilatation catheters often are used in conjunction with another tubular guide member through which the dilatation catheter is inserted and guided to the desired location in the body lumen of the patient. For example, the aforementioned Gruntzig Patent illustrates the use of a guide catheter in connection with percutaneous transluminal coronary angioplasty. Dilatation balloons used to treat a patient's gastrointestinal tract often are inserted into the patient through an endoscope. Endoscopes vary in length, depending on their intended purpose. For example, a typical multi purpose gastrointestinal endoscope may be of the order of four and one-half to five feet long and may be of the order of one inch diameter. It is formed from a plurality of articulated sections so that it is flexible. Controls, such as pull wires, are provided at the proximal end of the endoscope to control the shape of the distal end to steer and directionally control the endoscope. The endoscope typically has multiple channels for various functions and usually includes optical fiber channels to illuminate and permit visual observation of the patient's gastrointestinal tract. One or more channels, often only a few millimeters in diameter, also are provided through which instruments may be inserted into the patient such as, for example, miniature biopsy forceps, snares, needles, brushes, balloon dilatation catheters and others. An illustrative procedure may involve dilatation of the esophagus in order to enlarge a constriction caused, for example, by a tumor, esophagitis or other condition. In the procedure, the endoscope is passed through the patient's throat and into the esophagus. The progress of the endoscope is monitored visually through the fiber optic and illumination system. When the obstructed portion of the esophagus is reached, a dilatation catheter having a balloon at its distal end is passed through the instrument channel, with the balloon deflated, so that the balloon exits the distal end of the endoscope and passes through the obstruction. Once the balloon is placed within the obstruction, it is inflated to dilate the obstructed portion of the esophagus. The balloon must be deflated to a low profile in order for it to be passed through the instrument channel. Typically, the balloon is deflated by applying negative pressure to the balloon through an inflation/deflation lumen that extends from the proximal end of the catheter to the interior of the balloon.

Among the difficulties with dilatation balloons is the configuration that is assumed by the balloon when it is deflated. Typically, the balloon forms a pair of opposed, radially extending flat wings when it collapses under the influence of negative pressure. In order to insert the balloon into the instrument channel (or guide catheter lumen), the physician typically will manually wrap the wings about the catheter shaft and will insert the balloon catheter into the channel or guide catheter lumen in that configuration. The reduced profile also facilitates insertion of the balloon end of the catheter through the constriction. After the balloon has been inflated to perform the dilatation, it typically is deflated and, when that is done, it tends to assume the two wing configuration. The wings typically extend diametrally a distance substantially larger than the diameter of the channel. If it is desired to leave the endoscope in place and withdraw the dilatation catheter through the channel, that may present problems if the wings fail to wrap about the catheter shaft as the balloon is drawn into the channel. The wings may become caught at the distal end of the channel or otherwise interfere with smooth withdrawal. Withdrawal of the catheter may be necessary when it is desired to change catheters during the procedure, for example, as when the physician decides that further dilatation with a larger diameter balloon is required.

The foregoing problem has not gone unrecognized. Attempts to deal with it are evidenced by patented devices which seek to provide a means to cause the balloon to be wrapped closely about the catheter shaft to form a reduced profile. See, for example, U.S. Pat. No. 4,292,974 to Fogarty. Although such devices may have had some limited success, there remains a need for a simple effective means to facilitate collapse of a dilatation balloon to a low profile.

SUMMARY OF THE INVENTION

In accordance with the invention, a balloon for a dilatation catheter is formed to have a longitudinally fluted configuration when relaxed. When inflated, the flutes expand so that the balloon forms a cylindrical configuration needed for dilatation. When the inflation pressure is removed and the balloon is aspirated, the balloon contracts to its fluted configuration. The flutes, in effect, serve as partial preliminary folds so that when the balloon is withdrawn through the channel, it will continue to fold further along the longitudinal flutes. In accordance with the present invention, the flutes are arranged so that the balloon will fold to define at least three wings.

Another object of the invention relates to the method for forming the fluted balloon. The balloon is formed from a polymeric material, such as polyethylene terephthalate and may be formed in accordance with the method described in U.S. Pat. No. 4,490,421 to Levy. The balloon has a cylindrical main portion with cones on each end and cylindrical mounting collars on the ends of the cones. After the balloon is formed, as in the procedure described in the Levy patent, the balloon then is stretched longitudinally by gripping the mounting collars and pulling them in opposite directions to tension the balloon. Simultaneously with the tensioning, the balloon is evacuated. Such evacuation and tensioning causes the balloon to be stretched to form a plurality of longitudinally extending flutes. While holding the balloon in the fluted configuration, the balloon is heated to between about 180° F. to 220° F. and then is cooled to permit it to retain the fluted shape. The balloon then can be mounted on the catheter and other catheter manufacturing operations can be completed.

It is among the general objects of the invention to provide a new balloon configuration for a dilatation catheter which incorporates an improved means for collapsing the balloon to a low profile.

Another object of the invention is to provide a catheter having such a balloon.

A further object of the invention is to provide a dilatation balloon having a plurality of flutes.

Still another object of the invention is to provide a dilatation balloon and catheter utilizing such balloon in which the catheter collapses in a manner that defines at least three wings.

Still another object of the invention is to provide a method for forming such a fluted balloon.

DESCRIPTION OF THE DRAWINGS

The foregoing and other objects and advantages of the invention will be appreciated more fully from the following further description thereof, with reference to the accompanying drawings wherein:

FIG. 2 is an illustration of the manner in which the prior art dilatation balloon collapses to form a pair of diametrally opposed wings;

FIG. 3 is a somewhat diagrammatic sectional illustration of a catheter having a balloon of the present invention;

FIG. 4 is an end view of the distal end of the catheter of the present invention with the balloon inflated;

FIG. 5 is a sectional illustration through the balloon illustrating the manner in which it forms at least three wings when collapsed under negative pressure;

FIG. 6 is a side elevation of the balloon in a collapsed configuration;

FIG. 6A is an end elevation of the balloon as shown in FIG. 6;

DESCRIPTION OF THE PREFERRED EMBODIMENT

Figure 1:
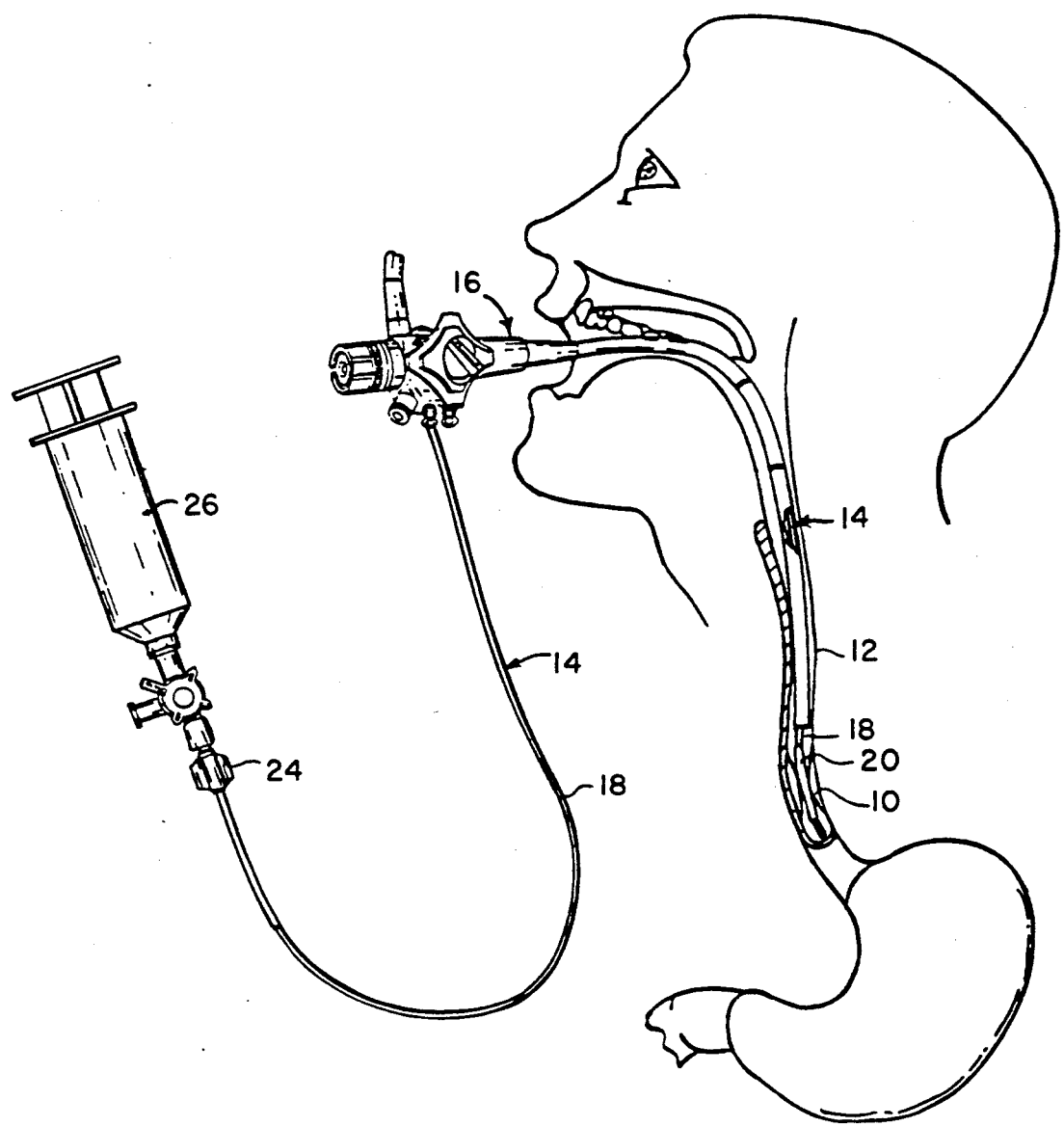
FIG. 1 is an illustration of a patient having an obstructed esophagus with an endoscope and dilatation catheter placed in readiness to perform a dilatation in the esophagus.

FIG. 1 illustrates a patient having a stenosis or constriction 10 in the esophagus 12 which is to be treated with a balloon dilatation catheter 14 inserted into the patient s esophagus 12 through an endoscope 16. The endoscope 16 typically includes one or more channels through which instruments, such as a dilatation catheter 14 may be passed. Typically, the endoscope 16 also carries optical fibers and illuminating means by which the interior of the body cavity under investigation may be examined visually.

The dilatation catheter 14 includes an elongate flexible shaft 18 having a dilatation balloon 20 carried at the distal end of the shaft 18. A lumen 22 (FIG. 3) extends through the shaft from the proximal end of the shaft to the dilatation balloon 20 at the distal end and communicates with the interior of the balloon 20. The proximal end of the shaft 18 is provided with a suitable fitting, such as a luer fitting 24 by which an inflation/deflation device, such as a syringe 26 (FIG. 1) may be connected. The tubular catheter shaft 18 may be formed from an appropriate plastic material such as a urethane compound. In the embodiment illustrated, the catheter is in the form of an esophageal balloon dilatation catheter. The dilatation balloon may be formed from a polymeric material such as polyethylene terephthalate and may be formed in a process as described in U.S. Pat. No. 4,490,421 to Levy. The balloon 20 includes an elongate cylindrical portion having a pair of tapered conical sections 28 at its opposite ends and proximal and distal collars 30, 32 extending from the ends of the conical sections 28.

In the esophageal catheter illustrated, an elongate wire 34 extends through the lumen 22 of the catheter. The proximal end of the wire 34 is encapsulated within the proximal fitting 24 as indicated somewhat diagrammatically at 36. The wire 34 extends distally beyond the distal end of the catheter shaft 18 and a distal tip 38 is attached to the distal end of the wire 34. The distal tip 38 may be formed from Dow Pellethane 2363-90R0120 polyurethane. The distal tip 38 is relatively soft and flexible. It serves to guide the distal tip of the catheter through the endoscope channel and also provides a soft flexible atraumatic tip when inserted into the patient. The distal collar 32 of the balloon is adhesively attached to the proximal end of the distal tip 38 and the proximal collar 30 of the balloon is adhesively attached to the distal end of the catheter shaft 18 by an appropriate adhesive such as cyanoacrylate. The wire 34 also is brazed to an internal metal ring 40 located at the distal end of the catheter shaft 18. The segment of the wire 34 extending between the metal ring 40 and the distal tip 38 serves to impart a slight longitudinal tension to the balloon when the balloon is deflated, thereby to assure that the balloon will be tensioned in a fluted configuration, described further below. When the balloon is inflated, the balloon may tend to contract which may cause the balloon segment of the wire 34 to bow somewhat.

By way of further example, the balloon of the esophageal catheter illustrated may be between 6 mm to 18 mm or more in diameter when inflated. The cylindrical midportion of the balloon may be of the order of 8 cm long. The end cones 28 may be of the order of 1.5 to 3 cm long. It should be understood, however, that the invention contemplates use in dilatation balloons other than for esophageal use and that the dimensions of such other dilatation balloons may vary from those illustrated and described herein.

FIG. 2 illustrates, digramatically, the cross-sectional configuration assumed by a typical dilatation balloon when suction is applied to the interior of the balloon to cause it to deflate. The balloon forms a pair of diametrally opposed wings 42 as the balloon 20 collapses. When the physician initially loads the endoscope with the dilatation catheter, it is relatively easy for him to manually wrap the wings 42 about the catheter shaft. The wings 42 thus assume a low profile configuration that permits easy insertion of the catheter through the narrow diameter channel in the endoscope. Although such a balloon can be extended from the distal end of the endoscope and can be inflated, some difficulty may be presented should it be desired to retract the balloon catheter through the endoscope channel. In particular, the diametrally opposed wings 42 may not tend to wrap about the catheter as the catheter is withdrawn back into the endoscope. Instead, the wings may catch on the distal opening of the endoscope channel.

In accordance with the present invention, the balloon is formed so that when deflated, it will tend to assume a fluted configuration having three or more wings. When such a balloon is collapsed, each of the wings is relatively short, in its radially extent, and more easily wraps about the catheter as the catheter is withdrawn through the endoscope channel. When inflated, the balloon assumes the cylindrical configuration illustrated in FIGS. 3 and 4.

FIG. 5 illustrates, diagrammatically, the cross section of the balloon when relaxed. The balloon tends to assume a configuration of alternating flutes 44 and wings 46. This configuration may be enhanced by incorporating the wire 34 and securing it near the proximal end of the balloon, as by attaching it to a metal band 40 in the illustrative embodiment, and by securing it at its distal end near the distal end of the balloon. The balloon may be mounted on the wire in a somewhat tensioned configuration such that the segment of the wire 34 extending through the balloon will tend to impart a longitudinal tension o the balloon thereby assuring its fluted configuration. When collapsed under the influence of suction applied to the catheter lumen, the balloon will assume a configuration as illustrated in FIGS. 6 and 6A in which the sides of each of the wings collapse against each other. It will be appreciated that the radial extension of each of the wings 46 of the fluted balloon is considerably less than the radial extension of the wings 42 in an unfluted balloon. With the fluted balloon configuration, the short wings are more easily folded as the balloon is drawn into the distal end of the endoscope channel. It should be noted that the flutes extend into the end cones 28 of the balloon as well as along the midportion of the balloon.

It should be noted that in addition to providing three or more flutes and wings, it is desired that the wall thickness of the balloon be relatively thin. By way of example, with the esophageal dilatation catheter described having a balloon diameter of 0.130" to 0.234" and a balloon length of 11 to 12 cm (cylinder length about 8 cm), an appropriate wall thickness of the balloon would be of the order of 0.0009" to about 0.0016", depending on the size of the balloon.

Figure 7:
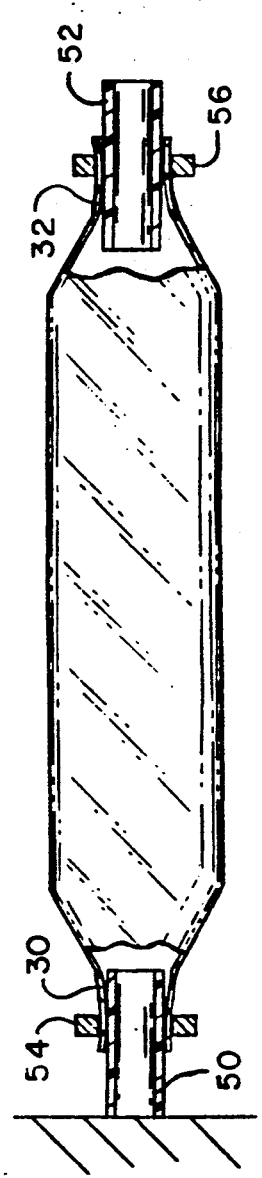
FIGS. 7 and 8 are diagrammatic illustrations of the steps involved in making the fluted balloon in accordance with the invention.
Figure 8:
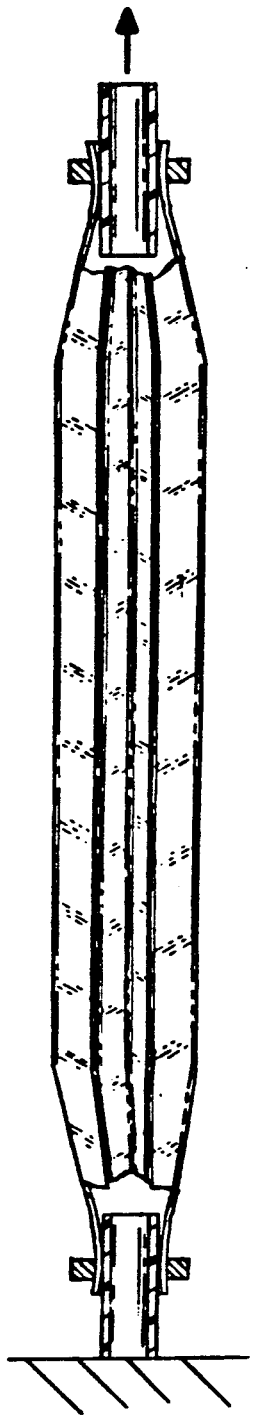

FIGS. 7 and 8 illustrate, diagrammatically, the manner and apparatus used to form the fluted balloon. The balloon is initially formed as described in the aforementioned U.S. Pat. No. 4,490,421. After the balloon is so formed, it is then mounted in a stretching device. The stretching device includes a stationary tubular member 50 and a movable tubular member 52. The balloon is mounted, by its collars 30, 32 on the tubular supports 50, 52. The collars 30, 32 are clamped securely to the tubes 50, 52 by ring clamps indicated schematically at 54, 56. With the balloon so mounted the balloon is evacuated by connecting one of the tubes, such as tube 52, to a source of suction and at the same time the movable clamp 52 is pulled to apply tension to the balloon. The applied tension causes a plurality of flutes to be formed lengthwise of the balloon and I have found that typically at least three, and usually four or more flutes are formed. With the balloon held in the tensioned configuration and while maintaining the balloon in its fluted configuration, the balloon is heated to about 180° F. to 220° F. After heating, the balloon is permitted to cool, while maintaining tension on the balloon. Once cooled, the balloon may be removed and it will retain its fluted configuration. The balloon then may be removed from the device and can be mounted on the catheter.

From the foregoing, it will be appreciated that the invention provides a balloon having a tendency to collapse in a fluted configuration forming at least three or more flutes. The radial extension of such flutes is relatively small. The flutes extend into the conical areas at the ends of the balloon. The fluted balloon more easily folds as it is withdrawn through a guiding channel, such as an endoscope channel or a guiding catheter.

Thus, it will be appreciated that the invention provides a new and improved fluted balloon configuration for a dilatation catheter by which the balloon more readily may be contracted to a low profile, as well as a method for forming such a fluted balloon.

It should be understood, however, that the foregoing description of the invention is intended merely to be illustrative thereof and that other modifications and embodiments may be apparent to those skilled in the art without departing from its spirit. For example, although the invention has been illustrated in connection with an esophageal dilatation catheter, it may be used with other balloon catheters, such as coronary dilatation catheters or peripheral blood vessel dilatation catheters.

Having thus described the invention what I desire to claim and secure by Letters Patent is:

1. A balloon dilatation catheter comprising:
   an elongate flexible tubular shaft having proximal and distal ends and at least one lumen extending through the shaft from its proximal to its distal end;
   a dilatation balloon mounted on the distal end of the shaft and in communication with the lumen;
   the balloon being preformed to have a collapsed configuration defined by at least three longitudinally extending flutes and alternating wings;
   a fitting at the proximal end of the shaft for connecting the lumen with an inflation and deflation device;
   a stiffening wire extending through the balloon and being rigidly attached to the distal portion of the shaft proximally of the balloon, the distal end of the wire having a catheter tip mounted thereon, the balloon being mounted at its proximal end to the flexible shaft and at its distal end to the catheter tip;
   the balloon being mounted on the catheter in a manner that when the balloon is not inflated, the wire will apply continually a longitudinal tension to the balloon, thereby tensioning the balloon in its fluted configuration, the balloon being substantially nonextendible longitudinally when under said tension.

2. A catheter as defined in claim 1 wherein the wire extends through the lumen of the shaft and is attached, at its proximal end, to the fitting.

3. A catheter as defined in claim 1 further comprising a rigid metal ring rigidly attached to the distal end of the catheter shaft, the wire extending through the metal ring and being securely attached thereto.

4. A catheter as defined in claim 1 wherein the balloon, when inflated, has a central cylindrical portion, end cones at each end of the central cylindrical portion and end collars at the end of the end cones.

5. A dilatation catheter as defined in claim 4 wherein when said balloon is deflated it forms said wings in a relatively short radially extending configuration and foldable to a low profile about the stiffening wire.

6. A catheter as defined in claim 5 wherein the balloon is inelastic.

7. A balloon as defined in claim 6 wherein the balloon is formed from polyethylene terephthalate.

* * * * *